US008880223B2

(12) United States Patent
Raj et al.

(10) Patent No.: US 8,880,223 B2
(45) Date of Patent: Nov. 4, 2014

(54) ANTHRO-CENTRIC MULTISENSORY INTERFACE FOR SENSORY AUGMENTATION OF TELESURGERY

(75) Inventors: Anil K. Raj, Pensacola, FL (US); Adrien M. Moucheboeuf, Pensacola, FL (US); Roger W. Carif, Cantonment, FL (US); Timothy L. Hutcheson, Pensacola, FL (US)

(73) Assignee: Florida Institute for Human & Maching Cognition, Pensacola, FL (US)

( * ) Notice: Subject to any disclaimer, the term of this patent is extended or adjusted under 35 U.S.C. 154(b) by 242 days.

(21) Appl. No.: 13/549,622

(22) Filed: Jul. 16, 2012

(65) Prior Publication Data

US 2014/0018819 A1 Jan. 16, 2014

(51) Int. Cl.
*A61B 19/00* (2006.01)

(52) U.S. Cl.
CPC .............. *A61B 19/22* (2013.01); *Y10S 901/09* (2013.01); *A61B 2019/2292* (2013.01); *A61B 19/28* (2013.01); *A61B 19/2203* (2013.01); *A61B 19/56* (2013.01); *A61B 2019/464* (2013.01); *Y10S 901/02* (2013.01); *Y10S 901/33* (2013.01)

USPC ............... 700/264; 700/258; 700/250; 901/2; 901/33; 606/130; 901/9

(58) Field of Classification Search
CPC .......... A61B 19/2203; A61B 19/5212; A61B 2019/223; A61B 19/22; A61B 19/56; A61B 2019/2234; A61B 17/00234; A61B 19/28; A61B 2017/00216; A61B 2019/2292; A61B 2019/464; Y10S 901/09
See application file for complete search history.

(56) References Cited

U.S. PATENT DOCUMENTS

| 7,835,498 | B2 * | 11/2010 | Bonfiglio et al. | 378/115 |
| 2009/0248036 | A1 * | 10/2009 | Hoffman et al. | 606/130 |
| 2010/0234857 | A1 * | 9/2010 | Itkowitz et al. | 606/130 |
| 2011/0238079 | A1 * | 9/2011 | Hannaford et al. | 606/130 |
| 2012/0154564 | A1 * | 6/2012 | Hoffman et al. | 348/65 |

* cited by examiner

*Primary Examiner* — Jason Holloway
(74) *Attorney, Agent, or Firm* — J. Wiley Horton

(57) ABSTRACT

A multisensory interface for a tele-robotic surgical control system. The invention allows the surgeon to use natural gestures and motions to control the actions of end effectors in the robotic surgical apparatus. Multiple feedback mechanisms are provided to allow the physician a more intuitive understanding of what is being controlled, along with a greater situational awareness. Prior art robotic end effectors are inserted into the patient through a small incision—as is already known in the art. The invention presents an improved method of controlling these effectors.

31 Claims, 18 Drawing Sheets

ANTHRO-CENTRIC MULTISENSORY INTERFACE FOR SENSORY AUGMENTATION OF TELESURGERY

STATEMENT REGARDING FEDERALLY SPONSORED RESEARCH OR DEVELOPMENT

This invention was made with governmental support under Award No. W81XWH-09-10617 awarded by the U.S. Army Medical Research and Materiel Command, Fort Detrick, Md., U.S.A.

CROSS-REFERENCES TO RELATED APPLICATIONS

Not applicable

MICROFICHE APPENDIX

Not Applicable

BACKGROUND OF THE INVENTION

1. Field of the Invention

The present invention pertains to the field of medicine. More specifically, the invention comprises a new user interface for controlling one or more surgical robots.

2. Description of the Related Art

Surgical techniques have evolved from "open" procedures in which the surgeon's hands entered the patient's body to endoscopic procedures in which a relatively small incision is made and visualization and manipulation tools are inserted through the incision into the body. The term "endoscopic" is used because visualization of the surgical site is provided via the insertion of a small optical device (originally some type of fiber optic image transmitter and now more commonly a small electronic camera).

The surgical tools that are used with endoscopic procedures tend to resemble older tools that were customarily used with open procedures. Although they are smaller, the end effectors and gripping portions of the endoscopic implements perform the same functions as their open predecessors. Tele-operated surgical robotic systems are now coming into widespread use, and these hold the promise of replacing the present endoscopic paradigm. Robotic surgical devices can provide greater accuracy and more degrees of freedom that a human-held endoscopic implement. However, the evolution away from open procedures to endoscopic procedures and ultimately to tele-robotic procedures is not without its drawbacks.

A surgeon performing an open procedure has the benefit of seeing precisely what his or her hands are doing. The surgeon can also feel the anatomical structures and the forces generated by the tools he or she is using. Some of these benefits were lost in the transition to endoscopic procedures. An even greater separation currently exists for tele-robotic procedures.

FIG. 1 shows a simplified depiction of a prior art robotic surgical apparatus 10. The device shown is similar to the DA VINCI surgical system marketed by Intuitive Surgical of Sunnyvale, Calif. Several support arms 18 are movably connected to column 16. Table 14 is also connected to column 16. The entire apparatus rests on base 12.

Table 14 may be movable in the x, y, and z axes to position the patient. One or more support arms 18 are movably attached to column 16. Joints 20 allows the support arms to articulate. Each support arm holds one or more end effectors 22. The end effectors are devices useful for medical procedures. Examples include electro-cautery devices, bone drills, and vascular clamps.

The actual end effectors may be quite small (millimeter-scale). They may also include one or more pivoting "wrists" near the end. This allows the end effector to be inserted through a small incision and then move in a variety of directions once inside the body. As those skilled in the art will know, the end effectors are capable of much more complex motion than would be possible with direct human manipulation of a passive device. In addition, the robotic surgical apparatus is able to move much more precisely than a human hand. The robotic surgical apparatus typically includes torque, position, velocity and strain sensors to maintain accurate closed-loop position and motion control.

Of course, a surgeon must control the robotic surgical apparatus. FIG. 2 shows a control station used for this purpose. Robotic control apparatus 24 is located remotely from the robot itself, though it will often be in the same room. Base 28 mounts stereoscopic view port 32, hand controller 30, and foot pedals 26. The surgeon typically sits in chair 44 in front of the control apparatus. A stereo endoscope on one of the robotic end effectors provides data to drive the stereoscopic view port 32. The surgeon places his or her eyes in front of the view port. The placement must be fairly close in order for the surgeon to adequately perceive the stereoscopic effect. The use of the stereoscopic view provides the surgeon with actual depth perception of the structures at the surgical site within the patient's body from a viewpoint fixed to the tip of the endoscope.

The surgeon controls the robotic end effectors primarily through the use of two hand controllers 30 and foot pedals 26. The use of the stereoscopic viewport and hand controllers compels the surgeon to sit in front of the control apparatus in a relatively fixed position. The controls themselves do not necessarily reflect the hand motions a surgeon is accustomed to making in an open or endoscopic procedure. FIG. 3 shows a prior art end effector 22 (a simple clamp). Movable jaw 38 moves toward fixed jaw 36 to clamp a desired object. Rotating joint 34 allows the movable jaw to be rotated about the roll axis to a desired orientation.

FIG. 4 shows one type of hand controller 30 that is used to control the operation of end effector 22. The surgeon moves grip 40 to adjust the position of the end effector. He or she then applies pressure to squeeze handle 42 in order to close movable jaw 38. It is possible to "map" the available control inputs to different functions so that a single input may be used to selectively control a variety of functions. A skilled surgeon may therefore use robotic control apparatus 24 to perform a wide variety of complex operations.

In studying the depiction of FIG. 2. however, the reader will appreciate a limitation inherent in this prior art approach. Traditional open surgery allowed the surgeon to be intimately in contact with the patient's anatomy. The surgeon employed the senses of sight, touch; and hearing to quickly gain and maintain situation awareness. As an example, a surgeon performing an open procedure might lean to one side to get a better look at a previously obstructed structure. This level of intuitive awareness was somewhat lost in the transition to endoscopic procedures. However, even for those procedures. the direct motions of the surgeon's hands translate to motions of the end effectors.

The robotic control apparatus shown in FIG. 2 presents a stark departure from the traditional paradigm. First, the surgeon is no longer near and oriented with respect to the patient. Second, there is no physical connection between the surgeon's hands and the end effectors. In fact, control software interprets the surgeon's input and uses that input to drive the motion of the selected effectors. In some aspects this "fly by wire" approach is beneficial (such as in smoothing out a trembling hand motion). But it fails to provide veridical force feedback, proprioception, and other useful sensations. Further, the prior art technique forces the surgeon to sit in an essentially static position. Robotic tele-surgery is presently recognized to be slower than comparable endoscopic procedures. Thus, the surgeon may be forced to remain in the static position for several hours.

On the other hand, tele-robotic surgery offers the advantage of not requiring a surgeon to actually be present at the site of the patient. In some instances this may be a great advantage. For example, a combat casualty could be treated by a variety of specialized surgeons who are not physically present. Each specialist only needs the ability to interface with the robotic surgical apparatus.

A better solution would combine the beneficial aspects of tele-robotic surgery with the more intuitive control environment of open and endoscopic procedures. The present invention seeks to provide such a solution.

BRIEF SUMMARY OF THE INVENTION

The present invention comprises a multisensory interface for a tele-robotic surgical control system. The invention allows the surgeon to use natural gestures and motions to control the actions of end effectors in the robotic surgical apparatus. Multiple feedback mechanisms are provided to allow the physician a more intuitive understanding of what is being controlled, along with a greater situation awareness. Prior art robotic end effectors are inserted into the patient through a small incision—as is already known in the art. The invention presents an improved method of controlling these effectors.

The surgeon's control inputs preferably assume the form of natural body motions. As an example, closing the hand can be used to control the closure of a micro-scale clamp. Moving the arm can be used to move an end effector in translation. Moving the body can be used to alter the vantage point of the surgical site.

The surgeon receives feedback as to the operation of the robotic end effectors through a variety of different devices. For example, visual feedback is augmented using a large video image displayed on a monitorplaced in front of the surgeon. The end effectors in this video image are approximately scaled to the physician's anatomy (such as a clamping device appearing to be roughly the same size on the video display as the surgeon's hand). An endoscopic depth-sensing camera is placed within the patient to provide an image of the surgical site. Software is used to map the surfaces seen within the patient. A motion-capture system senses when the surgeon leans left or right, or moves toward or away from the video display. The captured motions are used to alter the video display in order to create a simulated parallax effect. While the display remains two-dimensional, the simulated parallax effect allows the surgeon to intuitively perceive the depth dimension of the structures depicted.

Other feedback devices include a spatial audio display, avibro-tactile vest and electro-tactile arrays worn on the tongue and/or abdomen. The audio display can present sounds that appear to originate from different locations. The vest provides vibratory stimuli around the surgeon's torso. These devices are used to remind the surgeon of the location of effectors or anatomical structures (some of which may not be visible on the video display). The electro-tactile tongue array provides a high-resolution pattern of stimulation on the surgeon's tongue, while other devices can provide lower resolution or higher dimensional signals. This device can be used to provide force feedback, position information, or other desired information.

The invention creates an environment in which a surgeon controls the operation of the robotic end effectors using natural and intuitive motions. The surgeon also receives more complete feedback that is more naturally related to the operations being performed. This feedback approach does not introduce interference in the visual field or "fight" the surgeon's precise hand movements by back driving the control input devices. Further, the surgeon is free to move about and may assume a variety of comfortable working positions. This flexibility reduces fatigue.

Figure 1:
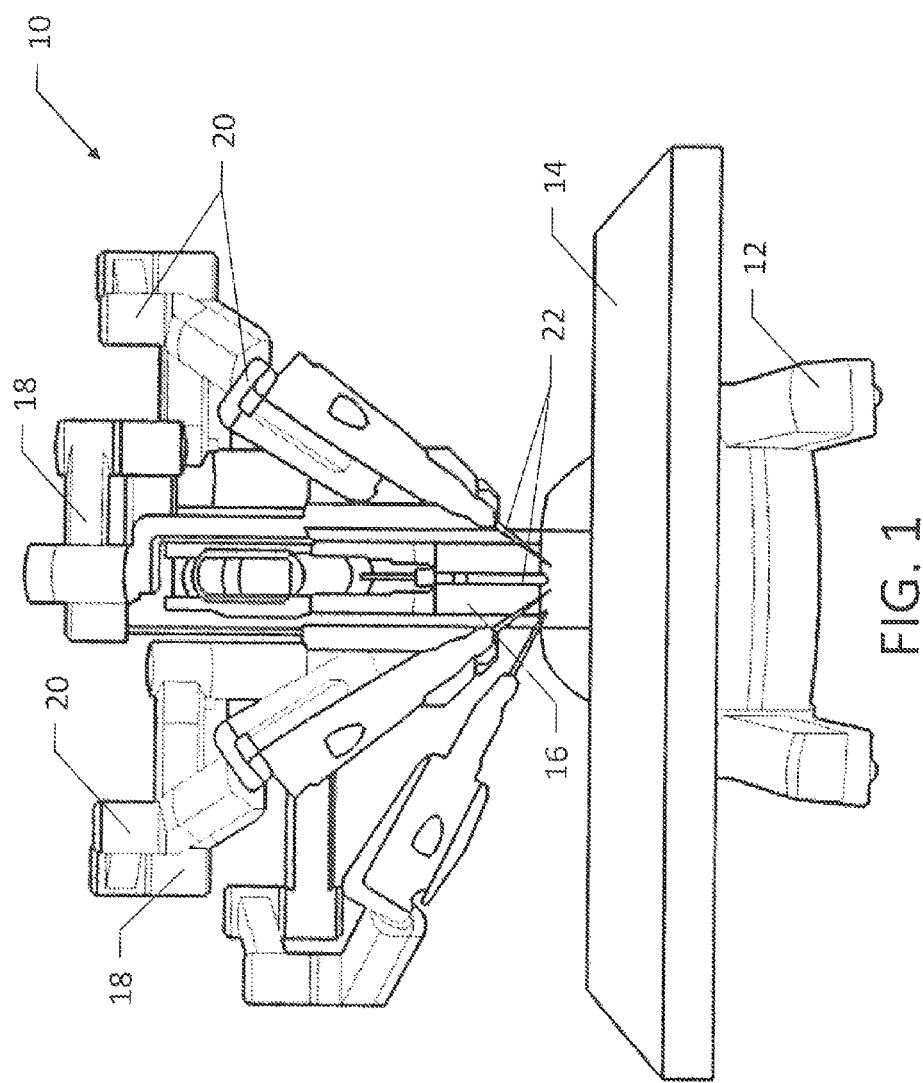
FIG. 1 is a perspective view, showing a prior art robotic surgical apparatus.
Figure 2:
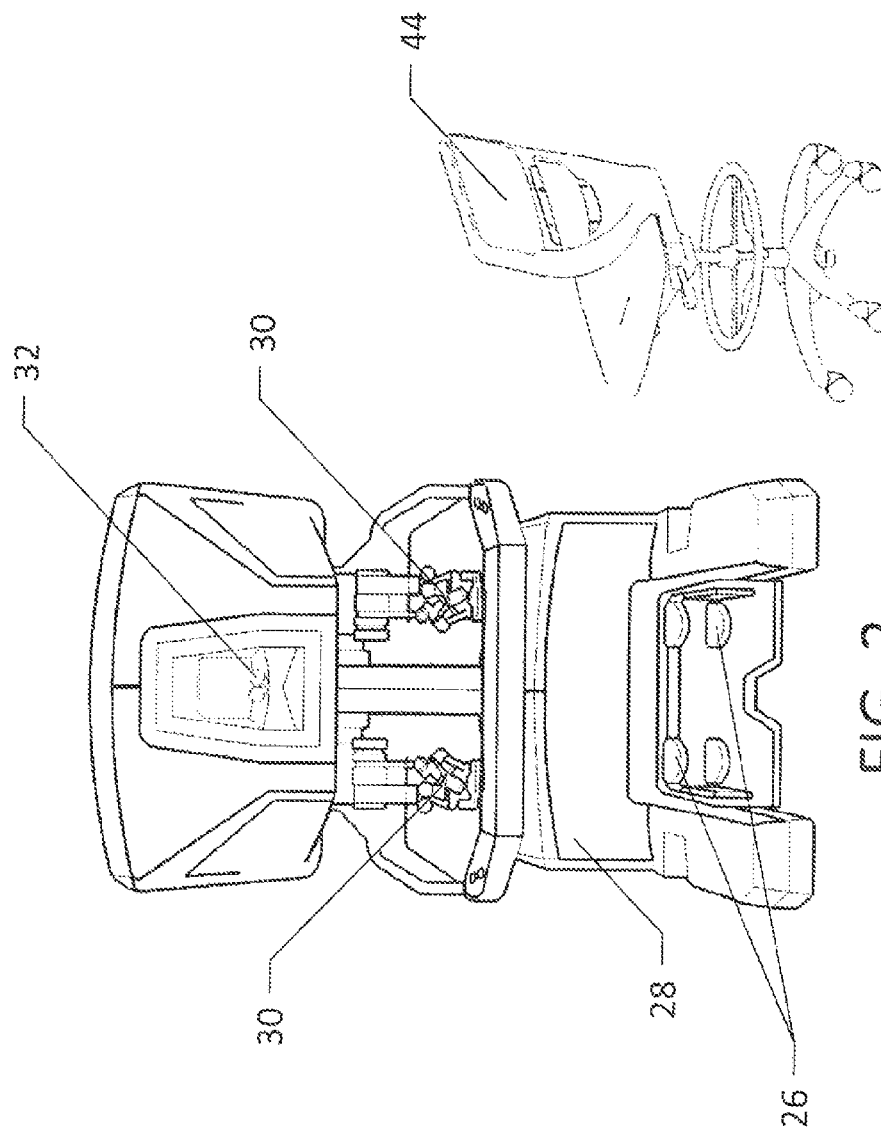
FIG. 2 is a perspective view, showing a prior art robotic control apparatus.
Figure 3:
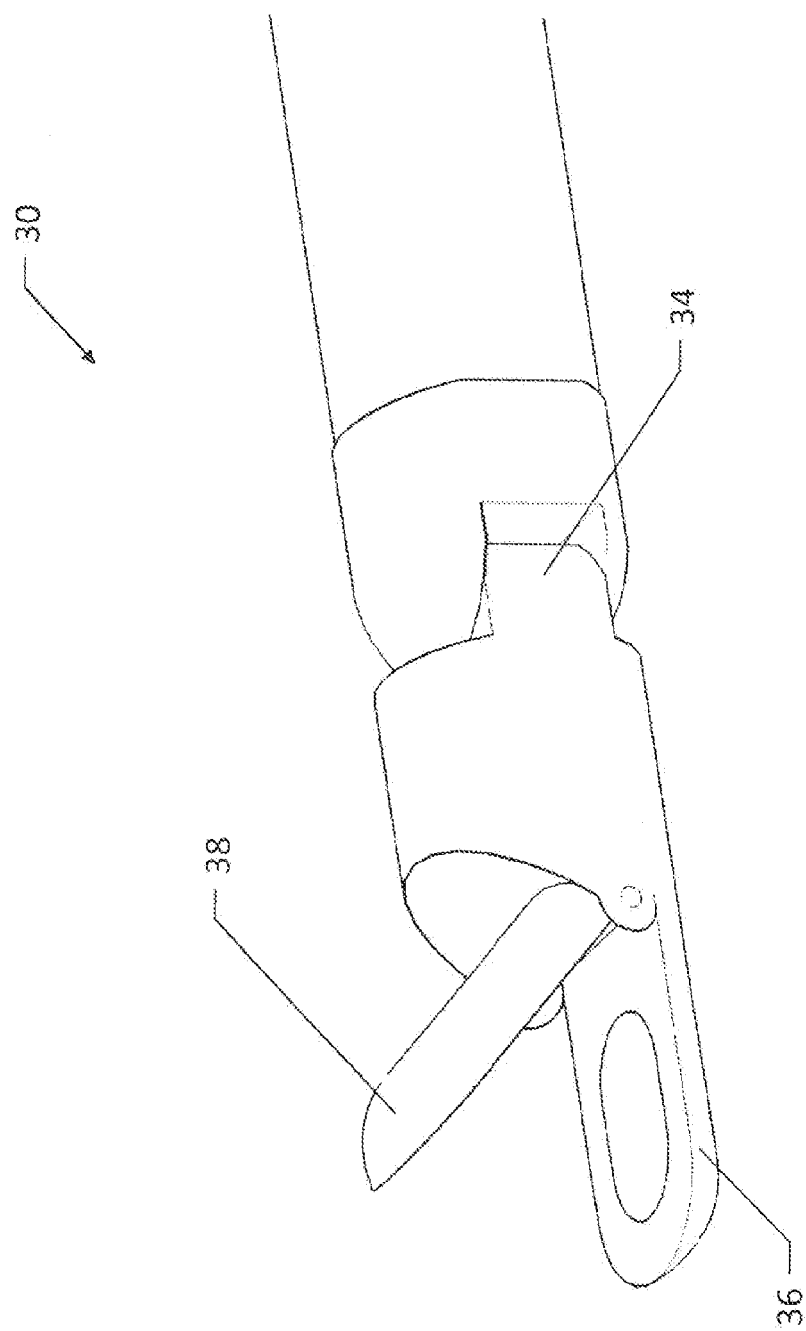
FIG. 3 is a perspective view, showing a simple type of end effector.
Figure 4:
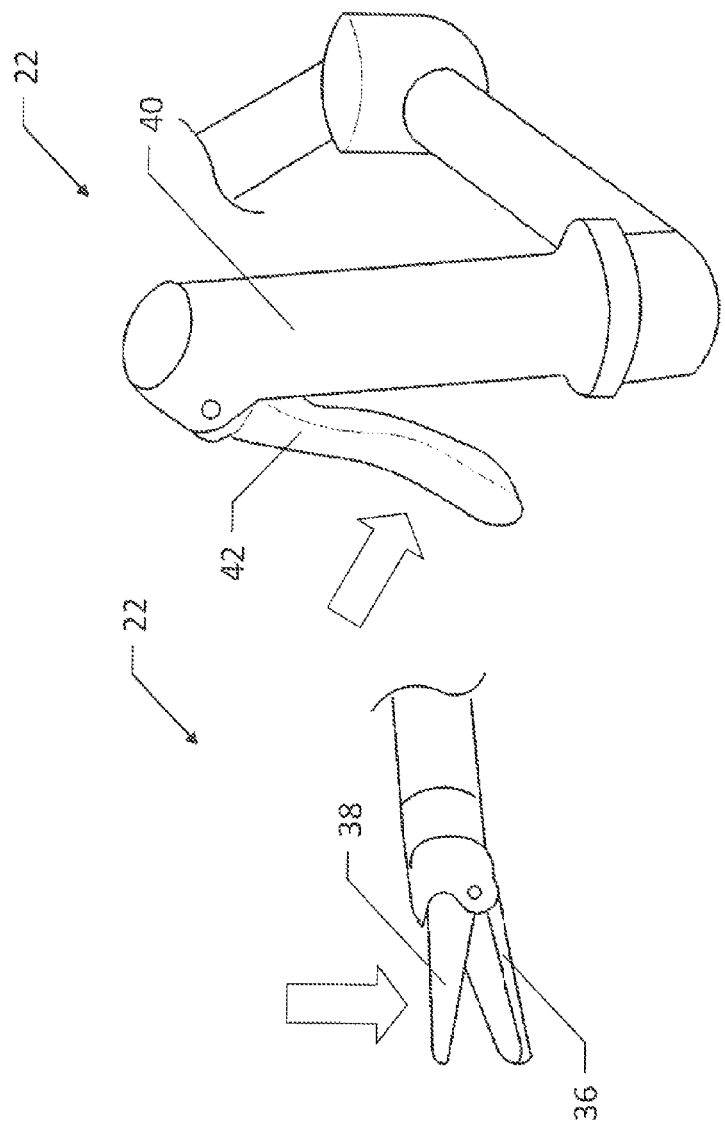
FIG. 4 is a perspective view, showing how an end effector may be controlled with a prior art hand controller.

| REFERENCE NUMERALS IN THE DRAWINGS | | | |
|---|---|---|---|
| 10 | robotic surgical apparatus | 12 | base |
| 14 | table | 16 | column |
| 18 | support arm | 20 | joint |
| 22 | end effector | 24 | robotic control apparatus |
| 26 | foot pedal | 28 | base |

| REFERENCE NUMERALS IN THE DRAWINGS | |
|---|---|
| 30 hand controller | 32 stereoscopic view port |
| 34 rotating joint | 36 fixed jaw |
| 38 movable jaw | 40 grip |
| 42 squeeze handle | 44 chair |
| 46 video monitor | 48 auxiliary monitor |
| 50 target vessel | 52 motion capture glove |
| 54 head motion capture system | 56 bodymotion capture system |
| 58 vibro-tactile abdominal display | 64 finger position sensors |
| 66 collector unit | 68 body position model |
| 70 vibro-tactile torso vest | 72 vibrotactile transducer |
| 74 parallax example | 76 stand |
| 78 depth-sensing camera array | 80 table |
| 82 roll | 84 box |
| 86 vessel | 88 fistula |
| 90 cutting tool | 92 suction tool |
| 94 electro-tactile array | 96 tongue |
| 98 pattern image | 100 abdominal image |
| 102 effector position tactile image | 104 no-fly zone |
| 105 first case display | 106 second case display |

DETAILED DESCRIPTION OF THE INVENTION

Figure 5:
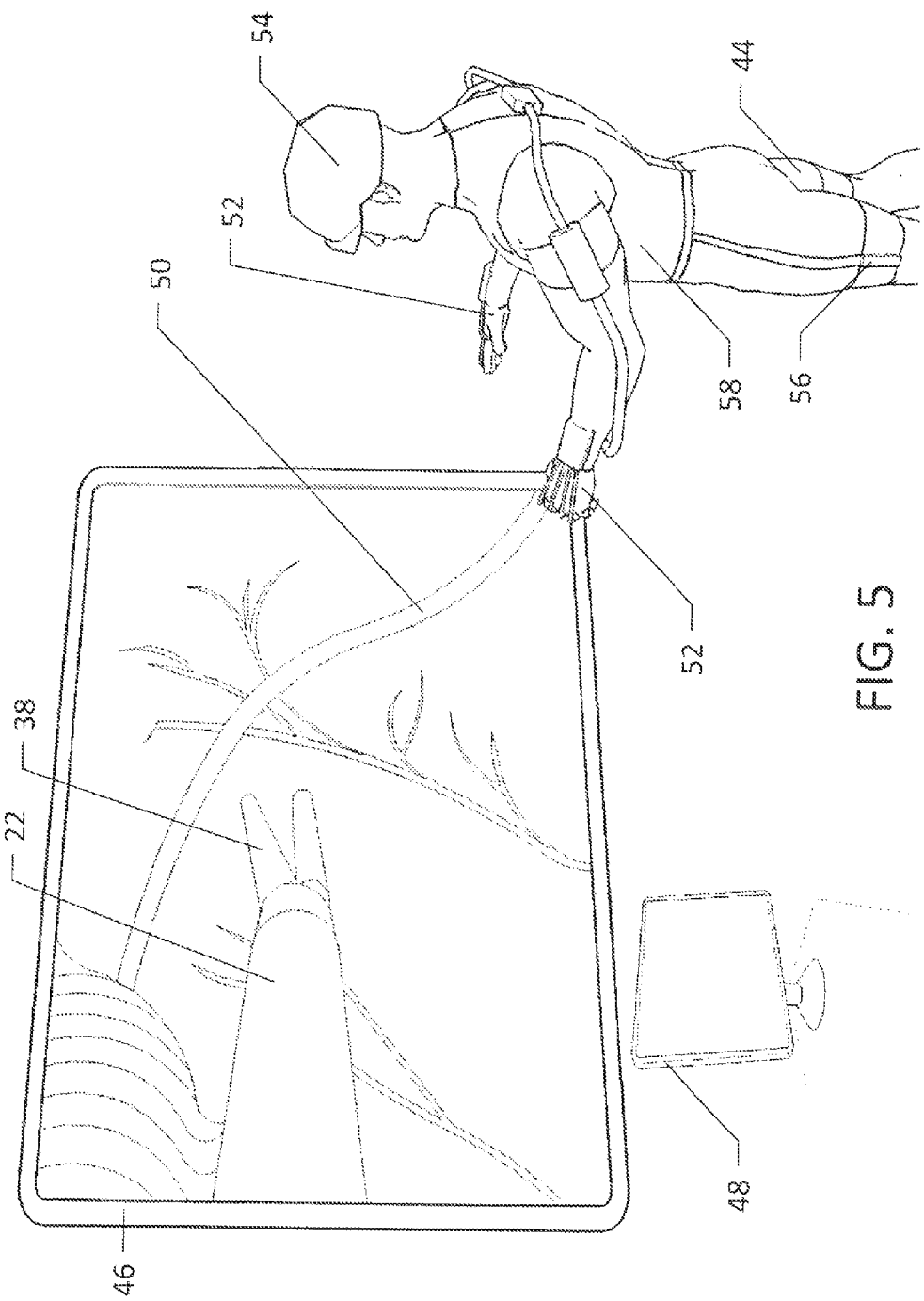
FIG. 5 is a perspective view, showing a robotic control apparatus constructed according to the present invention.

An over-arching goal of the present invention is to create a natural connection between a surgeon's body and the surgical implements being controlled. FIG. 5 shows a first embodiment which is constructed to achieve this over-arching goal. The figure shows the control apparatus and feedback mechanisms used to control a tele-robotic surgical device. These components allow surgeon 44 to control a robotic surgical apparatus such as depicted in FIG. 1.

FIG. 5 depicts a situation where one or more end effectors have been inserted into a small incision in a patient. A depth-sensing endoscopic camera system has also been inserted. Video monitor 46 provides a large depiction of what the camera system "sees." The camera system is oriented so that it points toward end effector 22 (The surgeon controls the orientation of the camera system). The surgeon is attempting to use the end effector 22 to clamp target vessel 50. He has thus far only been maneuvering the end effector into position.

Video monitor 46 is preferably a large monitor, having a diagonal dimension of 100 cm (39 inches) or more, or head mounted display with large field of view. In the preferred embodiment, the monitor has a diagonal dimension of about 180 cm (70 inches). The image from the camera system may be scaled ("zoomed") as desired. It is preferable to scale the image so that the size of the end effector components shown on the screen roughly equates to the size of the surgeon's anatomy that is being used to control those components. For example, the video image may be scaled so that the clamping apparatus including movable jaw 38 is roughly the same size as the surgeon's hand (meaning that the actual image of the clamping portion of the end effector on the video monitor is roughly the same size as the surgeon's hand).

A computer running control software is used to control the motion of the end effector, the camera system, and the video display. The same control software receives control inputs from the surgeon. The control inputs are preferably received as natural body movements. In the embodiment of FIG. 5, the surgeon inputs commands through various devices and receives feedback through various other devices. These devices will be listed and briefly explained, with a more detailed explanation of each to follow.

The input devices are actually worn by the surgeon in this embodiment. The input devices are: (1) a motion capture gloves 52 on each hand; (2) body motion capture system 56; and (3) head motion capture system 54.

Motion capture gloves 52 provide information regarding the position, orientation and movement of the surgeon's hands, fingers and thumbs. This system allows "gesture capture." Different gestures can be used as commands. As a first example, a clenched fist may be defined as a command which locks one or more end effectors in position. As a second example, making a "cutting scissors" gesture with the first and second fingers of the right hand might be defined as a command to actuate a cutting tool.

Body motion capture system 56 provides information regarding the position of the surgeon's body and limbs. For example a sweeping motion of the surgeon's left arm might be defined as a motion control command that laterally translates an end effector. A slow motion of the wrist might be used to directly control the motion of an end effector. In this mode, the motion of the end effector seen on the video monitor would directly follow the motion of the surgeon's wrist.

Head motion capture system 54 is preferably used to control pan and zoom features of the video display. As an example leaning the head to the left might be defined as changing the camera's vantage point to the left (explained in more detail subsequently).

The surgeon in FIG. 5 also receives feedback regarding the operation of the surgical robot from various devices. The feedback available preferably includes (1) video monitor 46; (2) auxiliary monitor 48; and (3) electro-tactile abdominal display 58. Video monitor 46 displays the surgical site. Auxiliary monitor 48 displays a wide variety of selectable information—such as which end effector is currently under the control of the surgeon's left hand as well as system settings. Vibro-tactile torso display 58 is a vest that includes an array of inward-facing vibratory transducers. These vibrate against the surgeon's abdomen in order to provide information, such as the location of effectors or warnings about encroachment toward anatomy that may not currently be visible on video monitor 46.

Having provided a brief explanation of some of the input and feedback devices, a more detailed explanation of each of these devices will be provided. The reader should bear in mind that the specific devices disclosed in detail do not represent the only type of device that could be used for these purposes.

Figure 6:
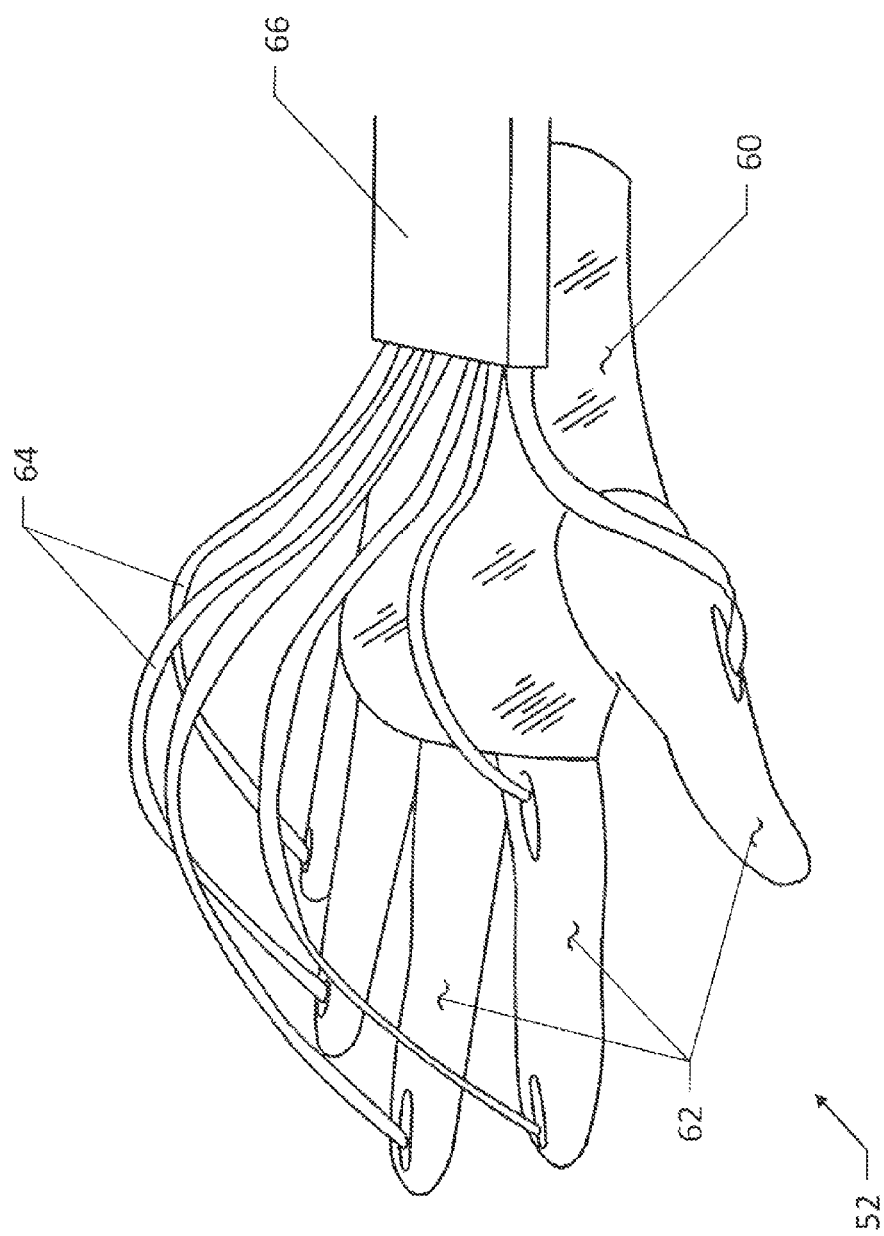
FIG. 6 is a detailed perspective view, showing a hand motion capture system used in the present invention.

FIG. 6 shows one embodiment for hand motion capture, the ShapeHandsold by Measurand, Inc., of Fredericton, New Brunswick Canada 52. In this embodiment, each digit of the hand includes a position sensor 64. The position data these sensors gather are passed to collector unit 66. Collector unit 66 collects the data, after which it is ultimately sent to the control software running on a computer. The control software is therefore given rapidly updated information as to the position of the joints within the hand.

There are other approaches available to gather this information. A second example is the use of video image capture. In this approach, a glove is worn over the hand. The fingers, hand and wrist are provided withsmallreflective spheres 62. One or more video cameras (generally at least two) are directed toward the surgeon's hands. These capture the image of the hands and then use triangulation or other known techniques to determine the position of each of the surgeon's digits. The gloves may be further enhanced to facilitate the image capture, such as by placing brightly colored regions on each of the joints and color-differentiated regions on each segment of each digit.

Whatever method is used to capture the digit position information, the information is ultimately used to compare the digit position against previously-defined gestures. A listing of all the possible pre-defined gestures is beyond the scope of this disclosure. However, a brief discussion of a few of these may aid the reader's understanding. The following gestures are preferably among the list of pre-defined gestures:

(1) A clenched fist is used to lock the effectors in position and suspend further input until they are unlocked;

(2) A reciprocating "cutting scissors" motion between the first and second fingers actuates a cutting end effector; and (3) Opening and closing the hand opens and closes a grasper proportionally.

Figure 7:
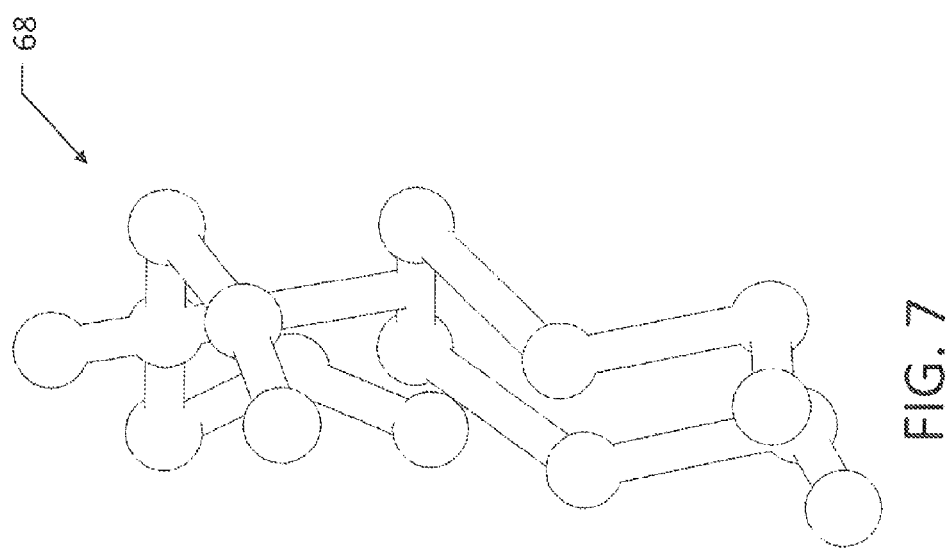
FIG. 7 is a perspective view, showing a body position model.

Returning now to FIG. 5, the reader will recall that the surgeon is wearing body motion capture system 56. An example of such a device is the SHAPEWRAP III sold by Measurand, Inc., of Fredericton, New Brunswick Canada. This device provides information concerning the position of the surgeon's limbs and torso. FIG. 7 depicts body position model 68, which is a "stick figure" model of the surgeon's present state based on the information received from body position capture system 56. Even of this is a relatively coarse model, it is still useful for entering pre-defined commands and for controlling the motion of components of the surgical robot. In fact the SHAPEWRAP III device provides an operationally useful measure of body position.

Figure 8:
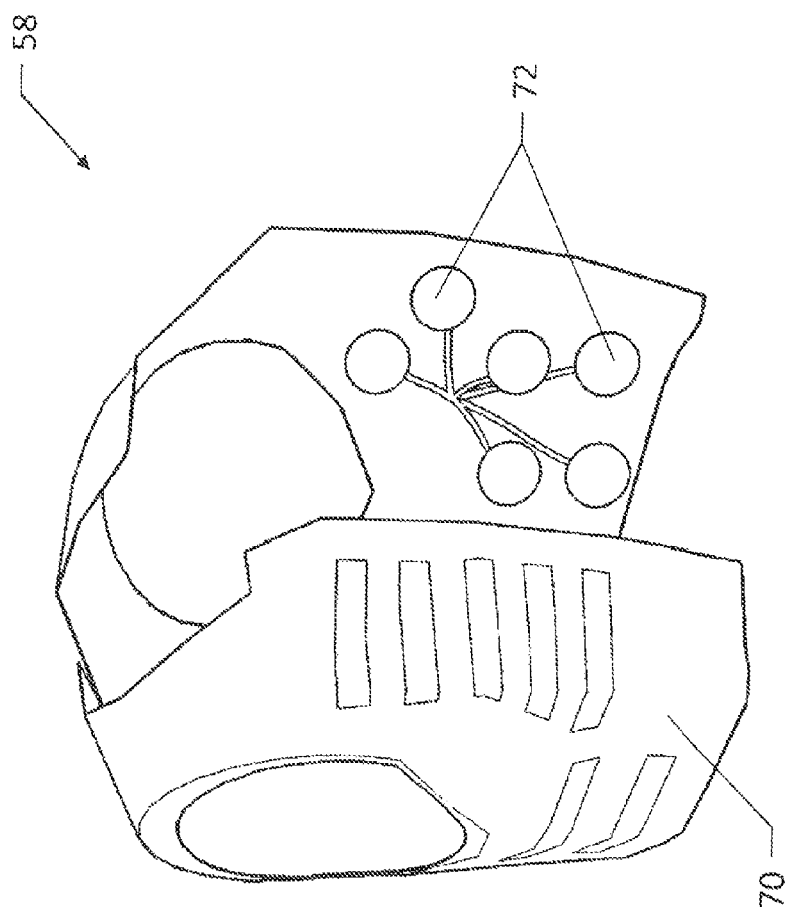
FIG. 8 is a perspective view, showing avibro-tactile torso display used in the present invention.

Returning again to FIG. 5, the reader will recall that the surgeon is wearing vibro-tactile torso display 58. This feedback device is shown in more detail on FIG. 8. Vest 70 is worn by the surgeon. It includes an array of inward-facing vibrotactile transducers (tactors) 72. The tactors are arrayed on both sides of the vest and extend around the body to create a three dimensional grid. An additional electro-tactile abdominal display, worn under the front of the vibro-tactile vest, provides a two-dimensional grid for data display. One example of such an array is the VideoTact manufactured by ForeThought Development in Blue Mounds, Wis.

The term "display" is used in a metaphorical sense. As an example, if an end effector is out of the field of the view of the display and is off to the right and down, a vibro-tactile transducer on the lower right side of the surgeon's torso will be fired. As a second example, if a surgeon has previously defined a region into which she does not want a tool to go (such as a boundary of the bladder) and the surgeon then seeks to move a tool into that area, some of the vibro-tactile transducers can be fired as a warning. It is preferable to have these "messages" be directionally specific. If the bladder is off to the right and the surgeon is moving a cutting tool in that direction, it is preferable to have the vibro-tactile transducers on the right side of the vest fire.

Figure 17:
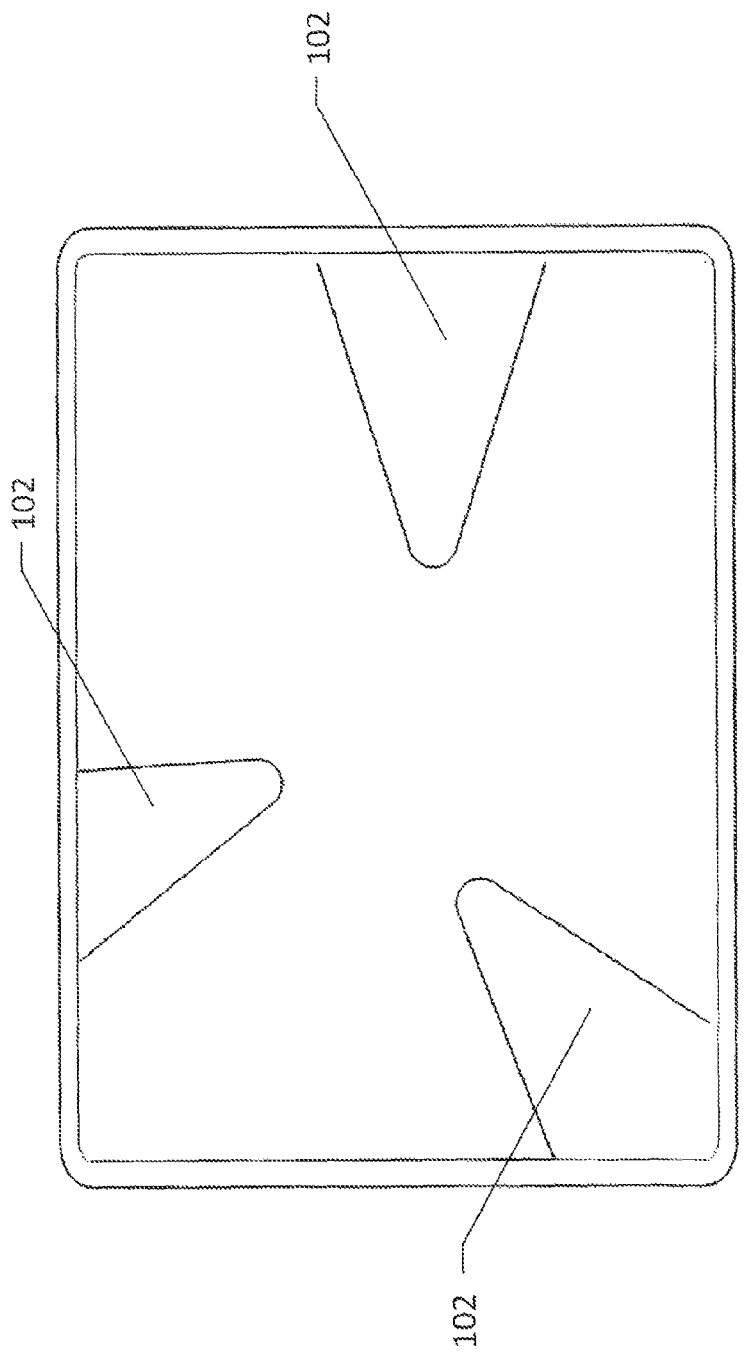
FIG. 17 is a depiction of the information provided by an electrotactile abdominal display.

The VideoTact array may be used to provide different types of feedback information. In a first version it is used to "display" the position of the different end effectors. A surgeon will generally be looking at one or two of the end effectors on the video display. One or more other end effectors may not be within the camera's field of view. However, it is important for the surgeon to be aware of their location in order to maintain situation awareness. FIG. 17 shows how this component may be used to provide an "image" of the location of the end effectors. In this example, three end effectors have been placed within the patient. Three effector images 102 are placed on the surgeon's abdomen by the repetitive activation of the electrode array. As each effector is moved, the "icon" of that effector is moved across the surgeon's abdomen. In this example, increasing forces on the shafts of the effectors, as may occur when a bony rib interferes with a desired end effector position change, result in a proportional increase in intensity of the relevant tactile icon. Abdominal image 100 assists the surgeon in maintaining situational awareness.

Of course, the signals received from the vest may not be directly related to the information they are intended to convey. However, because perception takes place in the brain and not at the end organ, the brain can learn to reinterpret the meaning of signals from specific nerves given appropriate feedback. Thus, with some training and practice, the surgeon can learn to interpret the input from the vibro-tactile transducers in a wide variety of ways.

It is not advisable to continuously activate a vibro-tactile transducer (such as repeatedly activating a transducer to indicate the static presence of an effector in one location). When processing and interpreting tactile data, specific traits of human sensation and cognitive processing (such as adaptation, habituation, or satiation to durative stimuli) may interfere with perception of persistent tactile stimuli. Adaptation occurs when a specific signal persists for an extended period of time (such as the tactile sensation of wearing a watch being filtered out by the peripheral and central nervous system). Habituation occurs when a signal repeats periodically (such as a ticking clock) and is no longer perceived. Satiation, also the product of prolonged stimulation, produces specific spatial distortions. It is possible to mitigate these effects by varying the intensity and duration of the stimulus (among other techniques). The control of the transducers in the vest preferably includes these mitigation techniques.

The operation of the depth-sensing camera system is a very important component of the present invention and it therefore warrants a detailed explanation. FIGS. 9-14 depict the operation of this system. Obviously the endoscopic depth camera that is to be inserted into the patient must be small. However, it is easier to understand the operation of a depth-sensing camera system with reference to larger objects. FIGS. 9-12 provide an explanation of a large-scale system viewing large objects. The same principles apply to a smaller system.

Figure 9:
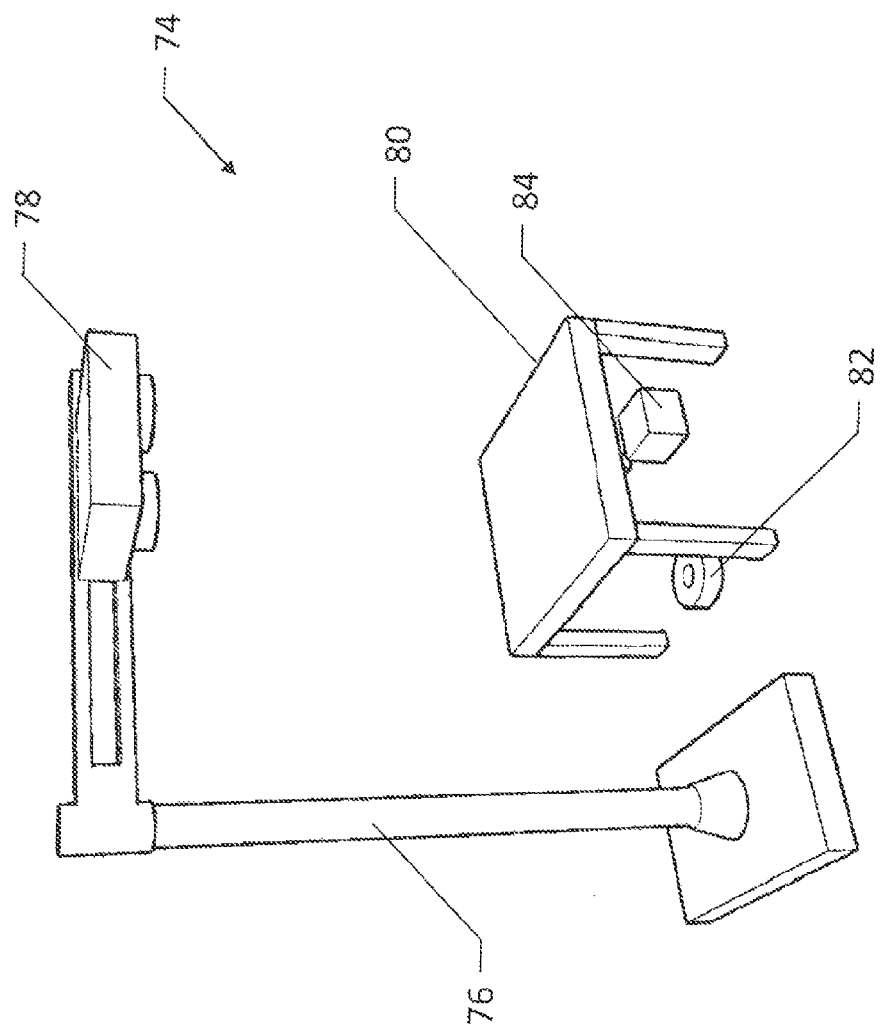
FIG. 9 is a perspective view, showing a depth sensing camera array and several objects within the camera's field of view.

FIG. 9 shows parallax example 74. In this example, depth-sensing camera array 78 is mounted on stand 76. The camera array is looking down toward table 80. Beneath the table are two partially occluded objects—roll 82 and box 84. The depth-sensing camera array is able to accurately measure and map objects within its field of view. An example of such a camera system is the KINECT camera and depth sensor marketed by Microsoft Corp. of Redmond, Wash., U.S.A. This camera and sensor system generates the data needed to generate three-dimensional models of the environment under study. This embodiment uses three KINECT cameras and a custom simultaneous location and mapping ("SLAM") algorithm.

The image ultimately produced by the depth sensing camera array and its associated software is a single image that appears to be taken from a single "apparent vantage point." The term "apparent vantage point" is used to mean a single point in space from which the image produced by the camera array appears to be taken.

The image produced by the camera array is a two-dimensional image, but one with very special properties. The image is not simply a transmission of what the camera array "sees." Instead, it is a depiction of a surface model the camera array and associated software has created. The surface model includes every object within the camera array's field of view. It also color mapped to the raw image data so that it appears very much like an unaltered video image. However, it is in fact a graphical depiction of a three-dimensional surface model. This fact allows the creation of a simulated form of parallax.

Figure 10:
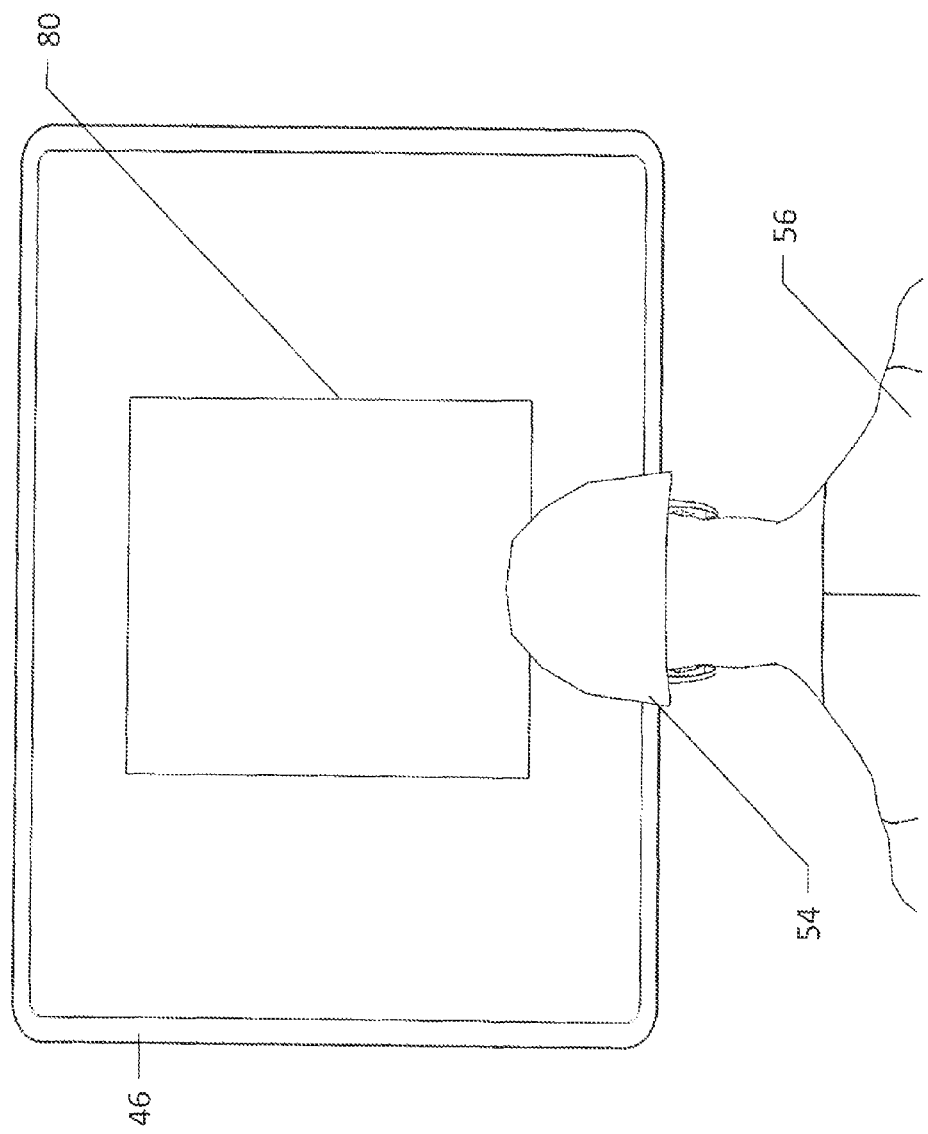
FIG. 10 is a perspective view, showing a surgeon viewing a video display.

The simulated parallax allows the two-dimensional image to behave very much like a three-dimensional image when it is combined with some of the surgeon's control input devices. FIG. 10 shows the depiction of the image created by depth-sensing camera array 78 and the associated surface mapping and imaging software. Table 80 appears on video monitor 46. Surgeon 44 is standing before the video monitor and the camera array has been directed to look straight at the center of table 80. The surgeon is wearing a light-weight head motion capture system incorporated into surgical cap 54. Head motion capture system monitors the position of the surgeon's head and feeds this information to the control software. An example of such a product is the OPTITRACK sold by NaturalPoint, Inc. of Corvalis, Oreg., USA.

In FIG. 10, the surgeon is standing upright looking at the center of the video display. This position is interpreted by the control system as requesting a central view point of the image produced by the depth-sensing camera array. Thus, table 80 is presented. However, because of perspective, the objects lying beneath the table (shown in FIG. 9) cannot be seen.

Figure 11:
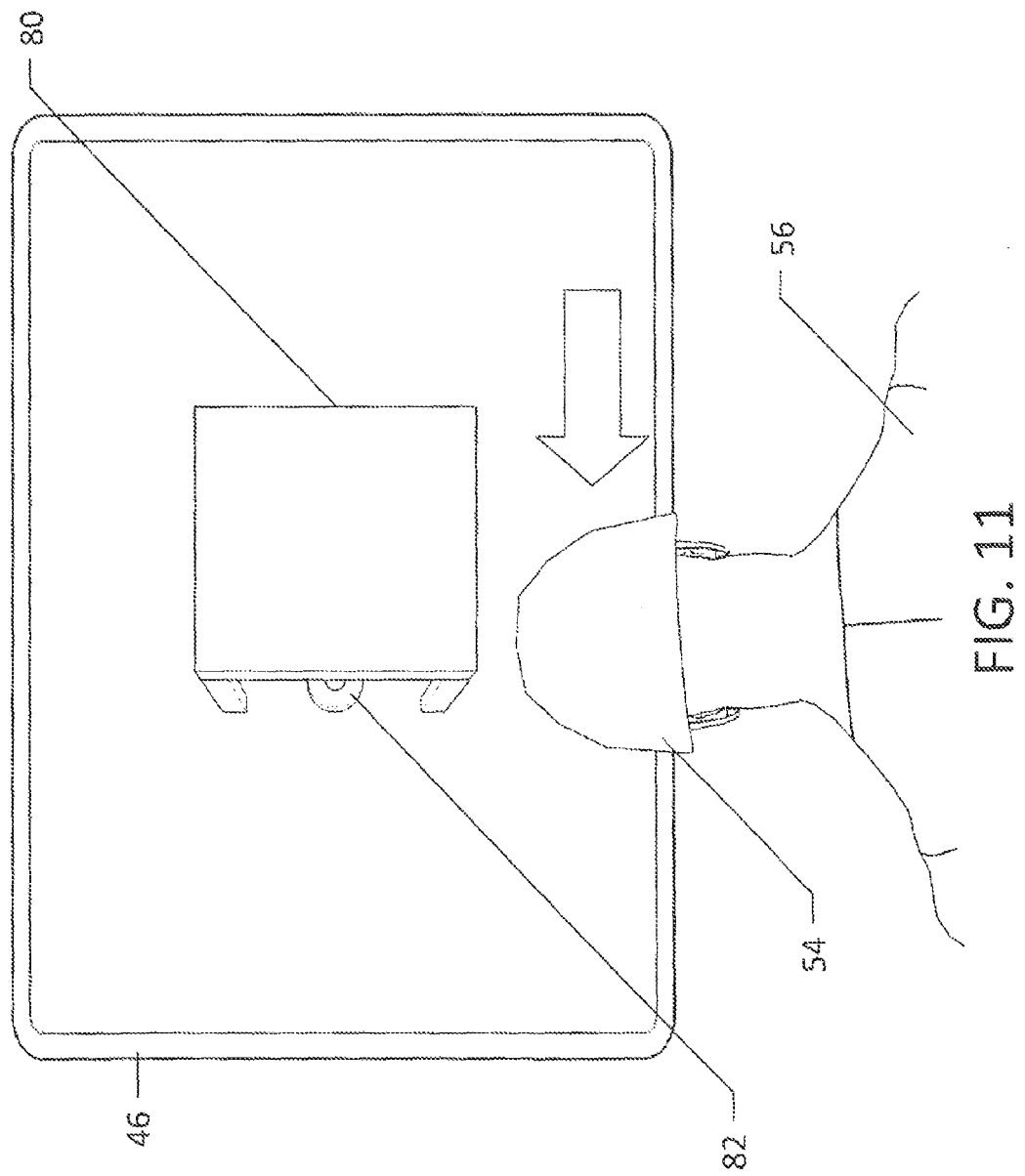
FIG. 11 is a perspective view, showing how the video is altered by the motion of the surgeon.

In FIG. 11, the surgeon has moved to the left. Head motion capture system 54 captures this movement. A person actually viewing an object would move his or her head to the left in order to "peek" around the object and see what might lie behind it. The image control software interprets the surgeon's move to the left as desiring this result. Accordingly, the software moves the "apparent vantage point" to the left and recomputes the display of the surface model it has mapped and stored. The perspective effects applied to table 80 shift as depicted and a portion of roll 82 becomes visible.

Figure 12:
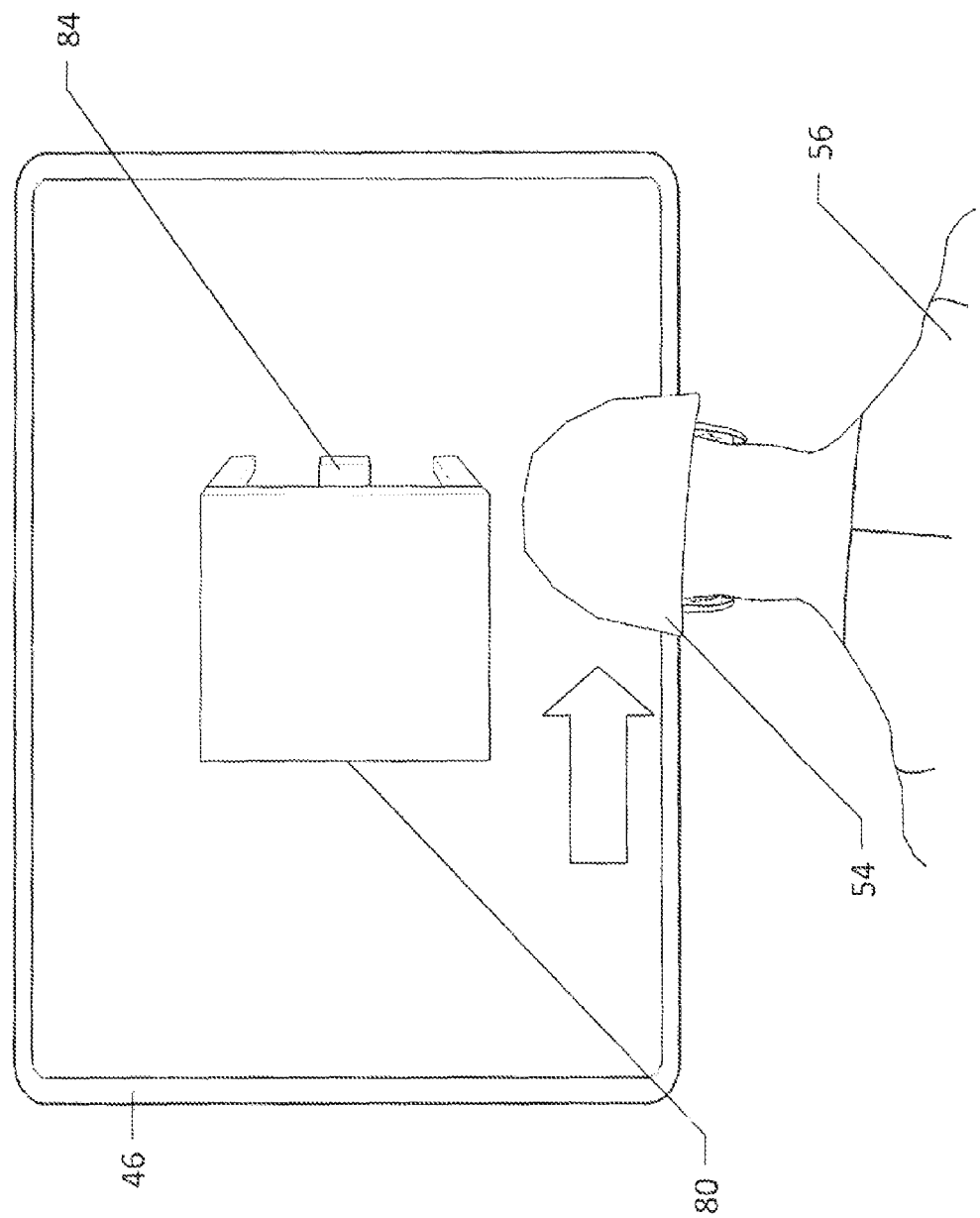
FIG. 12 is a perspective view, showing how the video is altered by the motion of the surgeon.

In FIG. 12 surgeon 44 has moved laterally to his right. The image control software interprets this motion as desiring a "peek" to the right. Accordingly, it moves the apparent vantage point to the right and recomputes the display. Table 80 is thereby shifted as shown. Roll 82 is no longer visible but a portion of box 84 becomes visible. The simulated parallax feature is not limited to panning left and right. The surgeon may also control panning up and down and at any desired angle. Small, high velocity movements used to "peek" around objects in the visual display exceed the velocity of the endoscope positioner and it may be undesirable to have the endoscope move faster for safety reasons. This method allows the visual image to move proportionally to head movement by manipulating the image in software. Slower, larger head movements needed to move to a different anatomic area, however, do cause mechanical movement of the endoscopic positioner. Areas not previously viewed and incorporated into the model are marked graphically as undetermined.

The same type of image capture and surface mapping technology can be applied to a small camera array capable of being inserted through an endoscope-sized incision. The small array includes the depth-sensing ability described previously. It builds complex surface models of the objects within its field of view.

Figure 13:
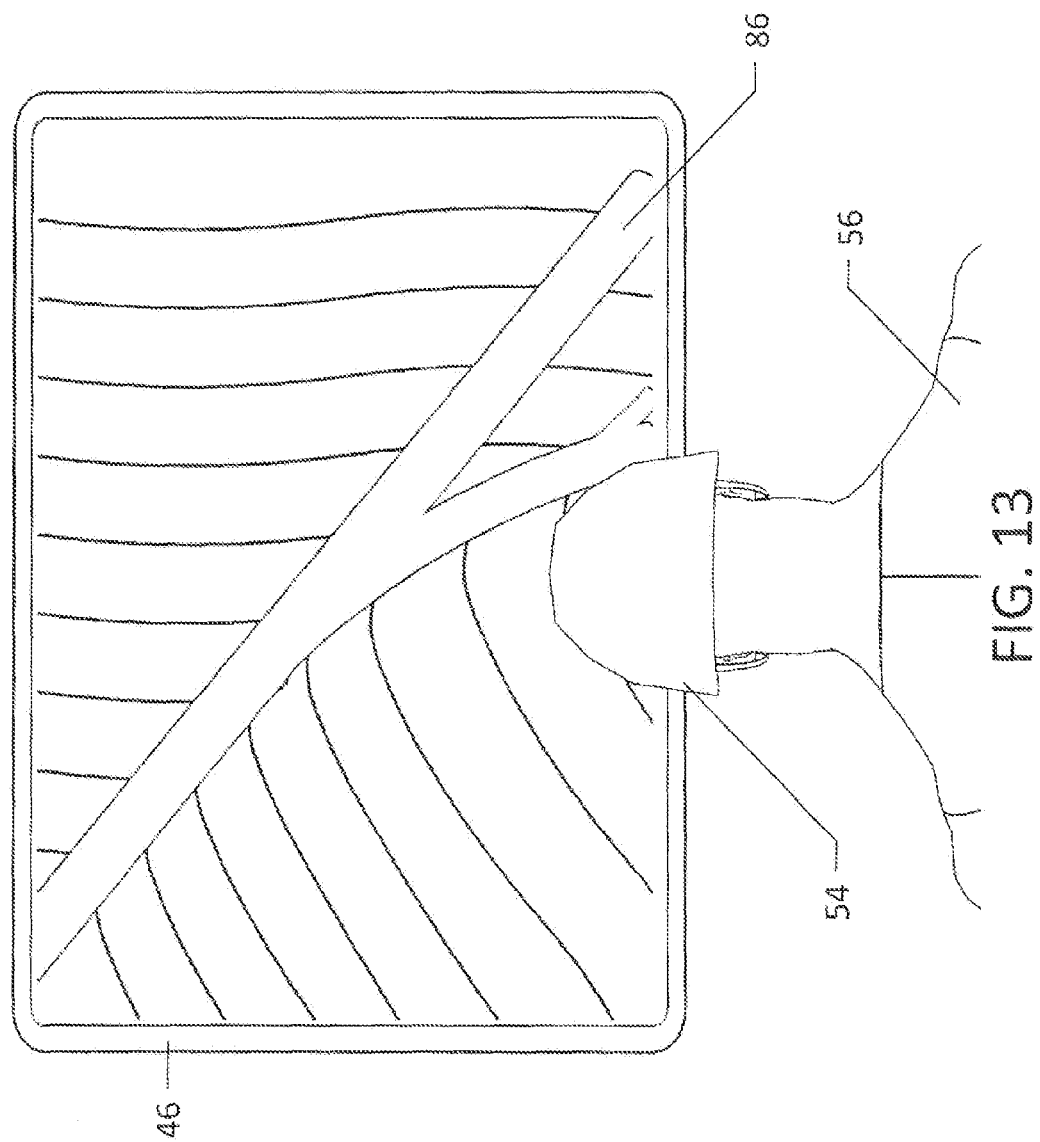
FIG. 13 is a perspective view, showing the display of an anatomical structure.
Figure 14:
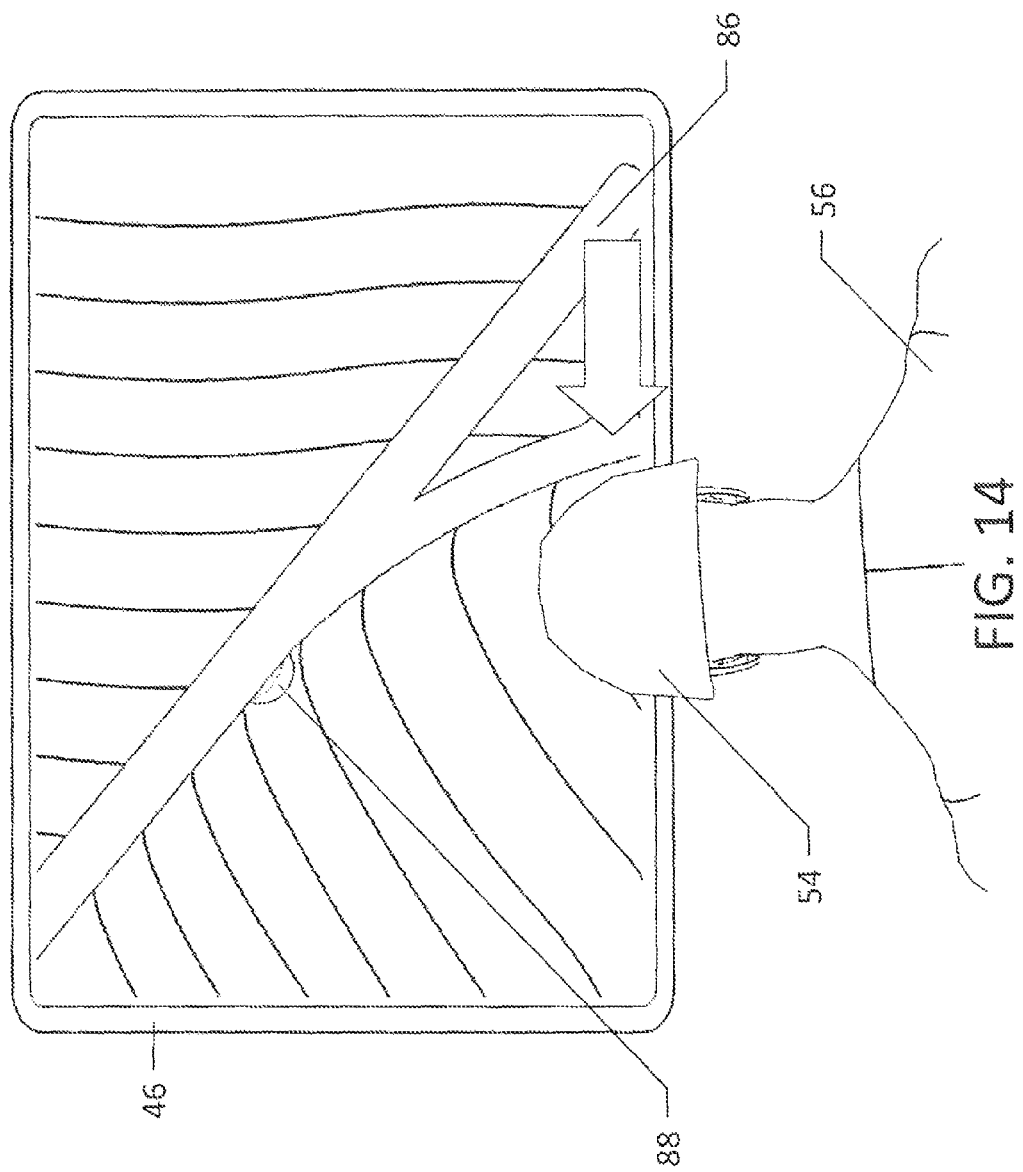
FIG. 14 is a perspective view, showing how the display of the anatomical structure is altered by the motion of the surgeon.

FIGS. 13 and 14 illustrate the operation of a small camera array during a surgical procedure. In FIG. 13, surgeon 44 is looking at a vessel 86 depicted on video display 46. Something is just visible to the left of the main juncture of the vessel, but it is not possible in FIG. 13 to determine what the object just behind the vessel is. In FIG. 14, the surgeon has leaned his head to the left in order to activate the simulated parallax capability. Not only does the video display pan to the left, but also the objects that are closer to the apparent vantage point translate laterally more than the objects that are farther away. The result is that vessel 86 moves farther than the underlying structures and fistula 88 becomes visible.

Actual parallax depends upon the vantage point of the viewer. When the viewer moves laterally, the phenomenon of actual parallax means that objects that are closer to the viewer appear to translate more than objects that are farther away (and distant objects do not appear to move at all). The same visual effect is produced by the software generating the display in FIG. 14. However, the parallax is "simulated" because it is not an optical effect but rather an effect generated by the software. The reader will recall that the depth-sensing camera array and associated software creates surface models of everything within its field of view. Multiple cameras are used so that geometry that is hidden from a single vantage point may be detected and mapped.

At any given instant, the display is displaying only part of the available surface map. It can selectively hide or show geometry that is occluded by the geometry of other objects lying closer to the apparent vantage point. But, by tying the selection and occlusion functions to the motion of the surgeon's head, a realistic simulation of parallax is generated. The image on the display is at all times two-dimensional. However, the surgeon may come to think of the display as three-dimensional since the inclusion of the simulated parallax is a very strong three-dimensional cue.

Figure 15:
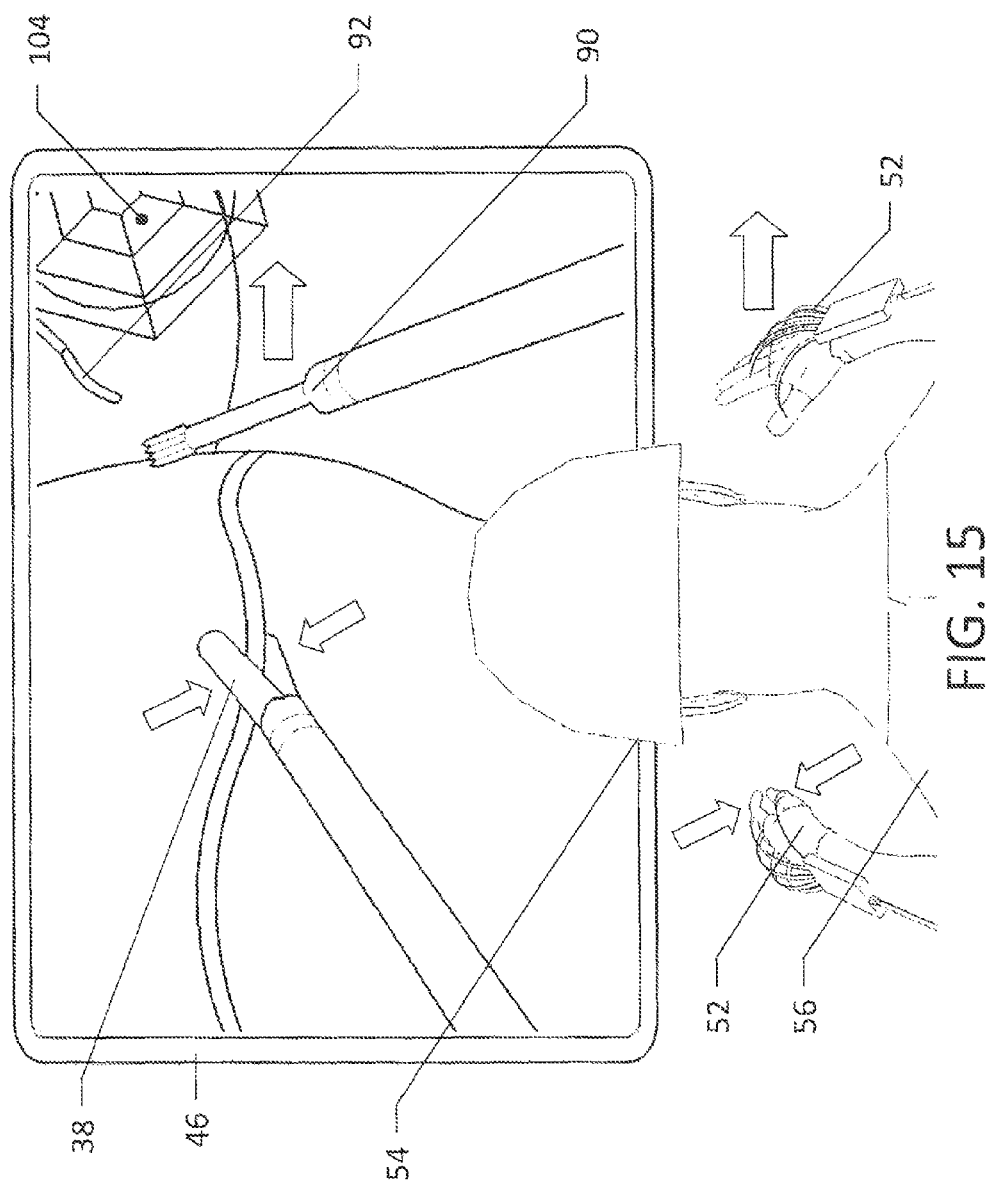
FIG. 15 is a perspective view, showing how the motion of the end effectors can be controlled by motions of the surgeon's body.

FIG. 15 shows one example of how the present invention may be used to control a robotic surgical apparatus. In this embodiment, movable jaw 38 has been mapped to the surgeon's left hand while cutting tool 90 has been mapped to the surgeon's right hand. By pinching the thumb and first finger of the left hand together, the surgeon controls the closing of movable jaw 38 proportionally. The input for this motion is via the motion capture glove on the surgeon's left hand.

By moving his right hand and wrist laterally, the surgeon moves cutting tool 90 laterally. The input for this motion is the body position capturing system. The image depicted is preferably scaled to match the surgeon's anatomy. As the surgeon moves his right wrist laterally, cutting tool 90 therefore moves at approximately the same rate across video monitor 46 as the surgeon's wrist moves through space.

The pan features of the video display are controlled via head motion capture system 54, as explained previously. The video display preferably also includes a zoom feature. In the preferred embodiment, the surgeon commands a "zoom in" by moving his head closer to the video display and a "zoom out" by moving his head farther away.

The use of a displayed surface model rather than a simple display of raw video data allows enhanced control functions. The surgeon may use her hands to define a series of points around a particular anatomical structure that must be protected. The system then displays a mesh model around this region. In FIG. 15, no-fly zone 104 is contained within a mesh previously defined by the surgeon. The control software will not permit tools to enter this defined region while providing a directional auditory or tactile stimulus as an encroachment warning.

The control of the end effectors appears to be direct for some commands—such as the lateral movement of cutting tool 90. In other words, the cutting tool appears to move directly as the surgeon's wrist is moved. This is not actually the case, however. The control software interprets the inputs from the surgeon and then creates a fine increment, closed-loop motion control for the end effectors. The reader will recall that the robotic surgical device already includes the necessary motion control information. The control software preferably accesses this information to meaningfully translate the surgeon's input motions into the desired end effector motions.

This functionality is analogous to the "fly by wire" functionality used in aircraft control system. "Fly by wire" flight control software does not directly translate input control motion into aircraft control surface deflection. Rather, it attempts to discern the pilot's intent and then create control surface deflections that will achieve that intent.

A very simple example is a pilot in high-speed stationary flight. If the pilot wishes to execute a maximum-performance pull-up maneuver, she may actually pull a control stick to the full aft position. If the control system simply commanded "full up" on the aircraft's elevators, a structural "overstress" would result. Instead, the "fly by wire" flight control system perceives the pilot's intent (a maximum-performance pull-up) and partially deflects the elevators, with the deflection increasing as the airspeed is reduced.

The "fly by wire" control software used for the tele-robotic surgical device includes analogous functionality. As a surgeon moves her forearm laterally, involuntary tremors may occur. The software "understands" that the intent is smooth lateral motion and eliminates the tremors. The software preferably also removes other involuntary motions like sneezing. It is also useful in considering the operation of an area like no-fly zone 104. If the surgeon moves his forearm so that cutting tool 90 will enter the no-fly zone, the control system stops the motion of the cutting tool and issues an alert (such as a graphical message on the video display or an auditory warning).

The surgeon obviously has only two arms, but three or more effectors may nevertheless be controlled. In the example of FIG. 15, the surgeon has previously moved suction tool 92 in position and "parked" it. It will remain in that location until it is again engaged. Thus, it remains in position while the surgeon actively controls moveable jaw 38 and cutting tool 90. The embodiment allows the surgeon to maintain awareness of the position of the end effectors tactually, even if the camera is moved and they no longer appear on the monitor.

It is desirable to provide feedback in addition to those components depicted in FIG. 5. For example, it is helpful to have positional feedback regarding the state of closure of a component such as movable jaw 38. It is often possible to directly visualize the position of this component, but in other instances it will be difficult to see. The robotic surgical apparatus itself always has information regarding the position of the various components, the force feedback being experienced (such as the resistance force of a blood vessel when a clamp attempts to clamp it closed), and the velocity of motion of the various components. Thus, the information already exists within the surgical robot's motion control system. The challenge is determining an effective means of conveying this information to the surgeon.

Figure 16:
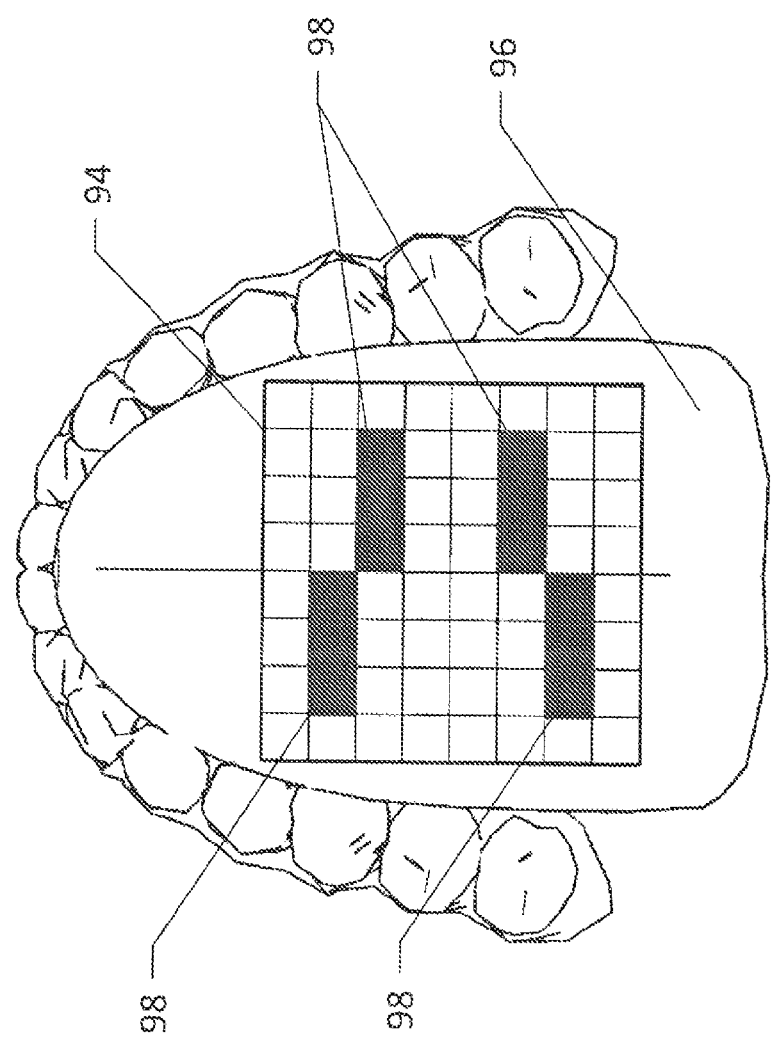
FIG. 16 is a plan view, showing an electrotactile array that can be used to provide information via the surgeon's tongue.

FIG. 16 depicts an electro-tactile array 94 that is placed on the upper surface of the surgeon's tongue 96. This device is held in placed by suitable features that are analogous to a mouth guard. An example of such a device is the BRAIN-PORT®, sold by Wicab, Inc. of Madison, Wis. U.S.A. The array contains a grid of individual electrical conductors which can apply a mild electrical stimulation to a small region of the tongue. The human tongue has the ability to detect these stimuli and to provide a high order of spatial differentiation. In fact, it is possible to use a grid that is much finer than the rather crude one depicted in FIG. 16.

Pattern image 98 is depicted as a series of pixels in the array. The black pixels represent an energized pixel. Many different patterns may be "displayed." Although the pixels are shown as being only black or white (a limitation of patent drawings), it is more common to provide finely variable levels of intensity in the array. As an example, increasing intensity may be used to convey increasing resistance to the closure of a clamping device. The example in FIG. 16 is being used to inform the surgeon of the present state of closure for movable jaw 38. The two bars on the left will move toward each other as the jaw closes, and will be aligned with the two bars on the right when full closure is achieved.

Motion within the array may be combined with varying signal intensity. Signal intensity increases as the force required to match the surgeon's grasp angle increases. This would be useful when the surgeon closes the movable jaw. As the jaw is closing, the surgeon feels the position reported on his or her tongue and can easily determine when the tissue has been grasped sufficiently by noting tracking the tactile intensity change. Rapid decrease of this intensity would indicate crushing of tissue. Of course, an electro-tactile array may be used to convey both position and feedback force, as well as other parameters.

One of the many advantages of tele-robotic surgery is the ability of a surgeon to work with many patients in a short period of time. In traditional surgeries—whether open or endoscopic—the surgeon must "scrub in" and "scrub out." Physical contact with each patient means that the surgeon must undergo a comprehensive disinfection before and after each procedure. Thus, when the surgeon finishes with a first patient, there will be considerable delay before a second patient can be addressed. And, there is no question of simultaneously working on multiple patients.

Figure 18:
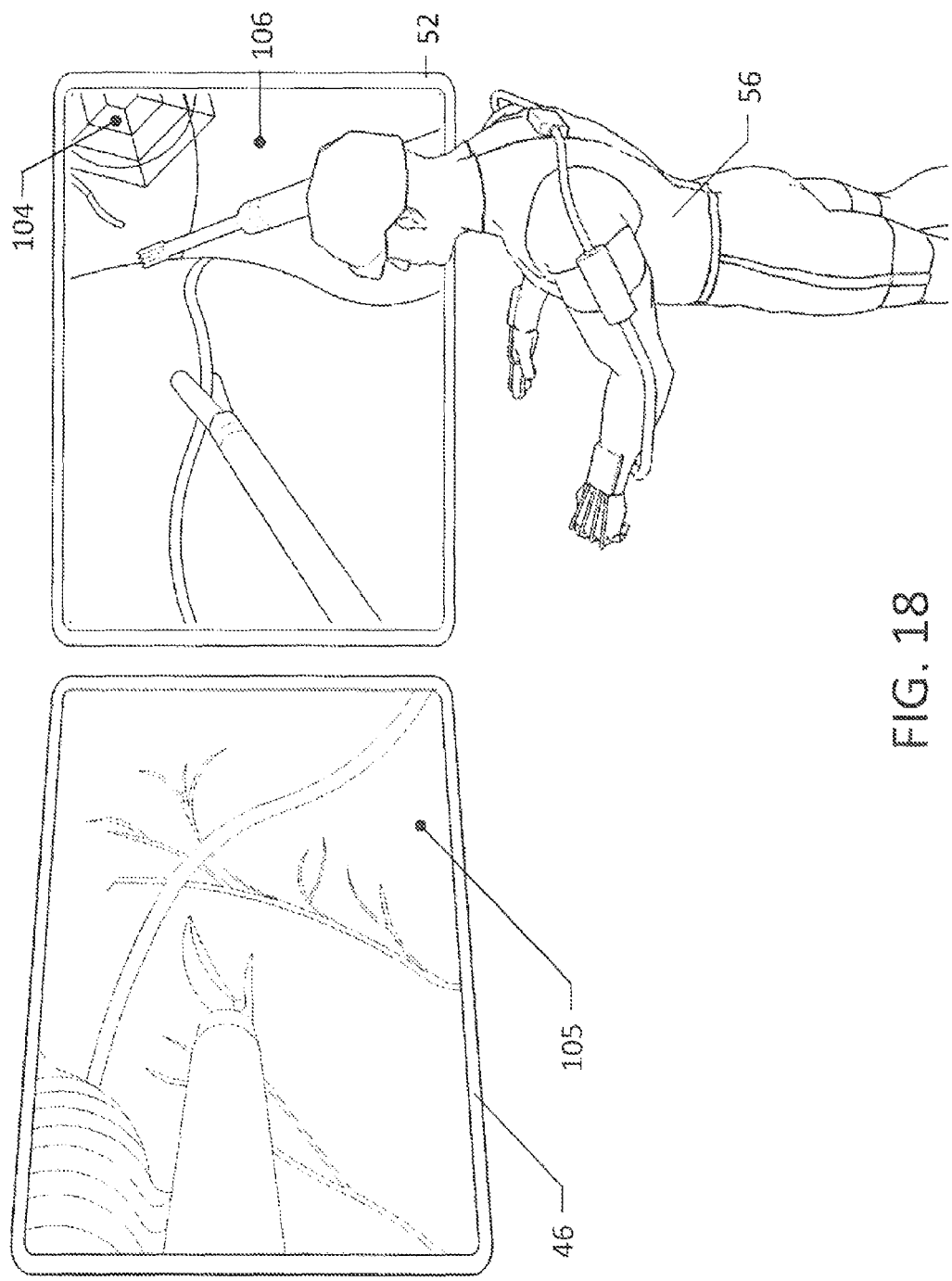
FIG. 18 is a perspective view, showing the use of the present invention by a single surgeon to perform procedures involving multiple patients.

This is not the case for tele-robotic surgery. Since there is no physical contact between the surgeon and the patient, there is no need for a "scrub in" or a "scrub out." In fact, the present invention easily allows the surgeon to work on multiple patients. FIG. 18 shows one embodiment of a multi-patient scenario. Two video displays 46 are provides. First case display 105 shows a procedure being performed for a first patient. Second case display 106 shows a procedure being performed for a second patient.

Surgeon 44 is given the ability to transfer back and forth between the two. The surgeon is currently viewing first case display 105. He may transfer control to the end effectors in the second case simply by turning and looking at the center of second case display 106. Of course, this method might allow an unintended transfer of control and it is better to provide a positive transfer step. One could accomplish this by defining a "double clench" (a clenching of both hands into a first) followed by an appropriate turn of the torso as a command to change to the other case and unlock the second robot. All commands and sensory feedback would be relative to the surgeon's current case. When transferring cases between surgeons, some data from the alternate case could be presented for monitoring purposes. The embodiment also allows more than one surgeon to share control of the end effectors much the way surgeons and their assistants perform open surgical procedures cooperatively.

The use of intuitive control of the robotic device allows many opportunities for automation of repetitive tasks. An example is the common task of suturing. Surgeons learn to suture rapidly with little thought. However, this task is difficult when performed remotely using a surgical robot. In the present invention the surgeon can enter the command gesture for "follow my example" before demonstrating the motion needed for a proper suture. The control software can then repeat the motion to create additional sutures as desired. The embodiment tracks position, orientation, velocity, force, spacing, etc., as the surgeon demonstrates the task. It then repeats the action, following a three dimensional trajectory defined by the surgeon until it reaches the end of the path or detects an error in one of the trained parameters (e.g., the force necessary to push the suture needle through the tissue increases above a threshold). In the case of an error, the software would stop the task and alert the surgeon. The software would automatically compensate for motion of the tissues, as occurs with "beating heart" procedures, using the three dimensional model created with the depth camera. "Follow my example" can be used for more complex macros using multiple tools and steps.

The control software can also be used to implement group positioning. This feature allows the surgeon to group two or more effectors together so that they may be jointly commanded. The group may then be moved from one location to another. Once in the new location, the group may be dissolved so that the effectors may again be commanded individually. This would be useful when, for example, the surgeon wishes to position multiple effectors in an anatomical location prior to initiating a phase of a procedure.

The preceding description contains significant detail regarding the novel aspects of the present invention. It is should not be construed, however, as limiting the scope of the invention but rather as providing illustrations of the preferred embodiments of the invention. As an example, some of the feedback techniques could be transferred to auditory cues (including directional differentiation). The surgeon might wear a set of stereo headphones in order to accurately receive these auditory cues. Approach toward a "no-fly-zone" could be related to the surgeon via a tone that increases in amplitude or frequency as the distance decreases. Many other variations are possible. Thus, the scope of the invention should be fixed by the claims presented, rather than by the examples given.

Having described our intention, we claim:

1. A method for allowing a surgeon to control a robotic surgical apparatus including an end effector, comprising:
   a. providing control software running on a computer;
   b. providing a gesture capture system, said gesture capture system capturing present location information for at least said surgeon s fingers and forearms;
   c. said gesture capture system providing said present location information for at least said surgeon's fingers and forearms to said control software;
   d. said control software controlling operation of said end effector;
   e. said control software using said present location information for at least said surgeon's fingers and forearms to control said operation of said end effector;
   f. providing a depth-sensing camera system, said camera system providing data sufficient to generate a three dimensional software model of structures within said camera system's field of view;
   g. using said camera system data to create a three dimensional software model of said structures within said camera system's field of view;
   h. providing a video display, including a pan function;
   i. displaying at least a portion of said three dimensional software model of said structures on said video display;
   j. providing a head motion capture system, said head motion capture system capturing present head location information fur said surgeon's head; and
   k. controlling said pan function on said video display using said head location for information for said surgeon's head.

2. A method for allowing a surgeon to control a robotic surgical apparatus as recited in claim 1, further comprising:
   a. providing an apparent viewpoint for said depth-sensing camera system; and
   b. providing a simulated parallax function as part of said video display, wherein when said pan function is activated, objects that are closer to said apparent viewpoint move a greater distance on said display that objects that are farther away.

3. A method for allowing a surgeon to control a robotic surgical apparatus as recited in claim 1, further comrising:
   a. providing a zoom function in said video display; and
   b. controlling said zoom function on said video display using said head location capture information for said surgeon's head.

4. A method for allowing a surgeon to control a robotic surgical apparatus as recite in claim 2, further comprising:
   a. providing a zoom function in said video display; and
   b. controlling said zoom function on said video display using said head location capture information for said surgeon's head.

5. A method for allowing a surgeon to control a robotic surgical apparatus as recited in claim 1, further comprising:
   a. panning said video display to the left when said surgeon's head moves left;
   b. panning said video display to the right when said surgeon's head moves right;
   c. panning said video display up when said surgeon's head moves down; and
   d. panning said video display down when said surgeon's head moves up.

6. A method for allowing a surgeon to control a robotic surgical apparatus as recited in claim 2, further comprising:
   a. panning said video display to the right when said surgeon's head moves left;
   b. panning said video display to the left when said surgeon's head moves right;
   c. panning said video display up when said surgeon's head moves down;
   d. panning, said video display down when said surgeon's head moves up;
   e. providing a zoom function in said video display; and
   f. controlling said zoom function on said video display using said head location capture information for said surgeon's head.

7. A method for allowing a surgeon to control a robotic surgical apparatus as recited in claim 1, further comprising:
   a. providing a zoom function in said video display; and
   b. initially setting said zoom function so that said end effector's display on said monitor is scaled to approximately match a forearm and a hand of said surgeon.

8. A method for allowing a surgeon to control a robotic surgical apparatus as recited in claim 1, further comprising providing specific defined positions for said surgeon's fingers which are interpreted by said control software as specific defined commands.

9. A method for allowing a surgeon to control a robotic surgical apparatus as recited in claim 8, wherein a clenched fist is defined as a command to lock a selected effector in position.

10. A method for allowing a surgeon to control a robotic surgical apparatus as recited in claim 1, further comprising:
    a. allowing said surgeon to control a second robotic surgical apparatus;
    b. wherein said robotic surgical apparatus is associated with a first patient and said second robotic surgical apparatus is associated with a second patient; and
    c. allowing said surgeon to toggle control between said robotic surgical apparatus and said second robotic surgical apparatus.

11. A method for allowing a surgeon to control a robotic surgical apparatus as recited in claim 1, thriller comprising:
    a. providing a sensory feedback display to said surgeon; and
    b. using said sensory feedback display to display a state of said end effector.

12. method for allowing a surgeon to control a robotic surgical apparatus as recited in claim 11, wherein said sensory feedback display is an electro-tactile array.

13. A method for allowing, a surgeon to control a robotic surgical apparatus as recited in claim 11, wherein said sensory feedback display is a vibro-tactile torso vest.

14. A method for allowing a surgeon to control a robotic surgical apparatus as recited in claim 11, wherein said state or said end effector is a position of said end effector.

15. A method for allowing a surgeon to control a robotic surgical apparatus as recited in claim 11, wherein;
   a. said end effector has a movable portion; and
   b. said state of said end effector is a position of said movable portion.

16. A method for allowing a surgeon to control a robotic surgical apparatus as recited in claim 15, wherein:
   a. said end effector is able to sense a force feedback for said movable portion; and
   b. said sate of said end effector is an amount of force feedback for said movable portion.

17. A method for allowing a surgeon to control a robotic surgical apparatus including an end effector, comprising:
   a. providing control software running on a computer;
   b. providing a gesture capture system, said gesture capture system capturing present location information for at least said surgeon's fingers and at least one wrist;
   c. said gesture capture system providing said present location information for at least said surgeon's fingers and said at least one wrist to said control software;
   d. providing specific defined Positions for said surgeon's fingers which are interpreted by said control software as specificdefined commands;
   e. wherein the posititin of said surgeon's fingers and said at least one wrist are used by said control software to control the veration of said end effector;
   f. providing a depth-sensing camera system, said camera system providing data sufficient to generate a three dimensional software model of structures within said camera system's field of view;
   g. using said camera system data to create a three dimensional software model of said structures within said camera system's field of view;
   h. providing a video display;
   i. displaying at least a portion of said three dimensional software model of said structures on said video display;
   j. providing a pan function for said video display;
   k. providing a head motion capture system, said head motion capture system capturing present head location information for said surgeon's head; and
   l. controlling said pan function on said video display using said head location information for said surgeon's head.

18. A method for allowing a surgeon to control a robotic surgical apparatus as recited in claim 17, further comprising:
   a. providing an apparent viewpoint for said depth-sensing camera system; and
   b. providing a simulated parallax function as part of said video display, wherein when said pan function is activated, objects that are closer to said apparent viewpoint move a greater distance on said display that objects that are farther away.

19. A method for allowing a surgeon to control a robotic surgical apparatus as recited in claim 17, further comprising:
   a. providing a zoom function in said video display; and
   b. controlling said zoom function on said video display using said head location capture information for said surgeon's head.

20. A method for allowing a surgeon to control a robotic surgical apparatus as recited in claim 17, further comprising:
   a. panning said video display to the right when said surgeon's head moves left;
   b. panning said video display to the left when said surgeon's head moves right;
   c. panning said video display up when said surgeons head moves down; and
   d. panning said video display down when said surgeon's head moves up.

21. A method for allowing a surgeon to control a robotic surgical apparatus as recited in claim l7, further comprising:
   a. panning said video display to the right when said surgeon's head moves left;
   b. panning said video display to the left when said surgeon's head moves right;
   c. panning said video display up when said surgeons head moves down; and
   d. panning said video display down when said surgeon's head moves up;
   e. providing a zoom function in said video display; and
   f. controlling said zoom function on said video display using said head location capture information for said surgeon's head.

22. A method for allowing a surgeon to control a robotic surgical apparatus as recited in claim 17, further comprising:
   a. providing a zoom function in said video display; and
   b. initially setting said zoom function so that said end effector's display on said monitor is scaled to approximately match a wrist and a hand of said surgeon.

23. A method for allowing a surgeon to control a robotic surgical apparatus as recited in claim 17, further comprising:
   a. providing a zoom function in said video display;
   b. initially setting said zoom function so that said end effector's display on said monitor is scaled to approximately match a wrist and a band of said surgeon.

24. A method for allowing a surgeon to control a robotic surgical apparatus as recited in claim 17, wherein a clenched first is defined as a command to lock a selected effector in position.

25. A method for allowing as surgeon to control a robotic surgical apparatus as recited in claim 17, further comprising:
   a. allowing said surgeon to control a second robotic surgical apparatus;
   b. wherein said robotic surgical apparatus is associated with a first patient and said second robotic surgical apparatus is associated with is a second patient; and
   c. allowing said surgeon to toggle control between said robotic surgical apparatus and said second robotic surgical apparatus.

26. A method for allowing a surgeon to control a robotic surgical apparatus as recited in claim 17, further comprising:
   a. providing a sensory feedback display to said surgeon; and
   b. using said sensory feedback display to display a state of said end effector.

27. A method for allowing a surgeon to control a robotic surgical apparatus as recited in claim 26, wherein said sensory feedback display is an electro-tactile array.

28. A method for allowing a surgeon to control a robotic surgical apparatus as recited in claim 26, wherein said sensory feedback display is a vibro-tactile torso vest.

29. A method for allowing a surgeon to control a robotic surgical apparatus as recited in claim 26, wherein said state of said end effector is a position of said end effector.

30. A method for allowing a surgeon to control a robotic surgical apparatus as recited in claim 26, wherein:

a. said end effector has a movable portion; and
b. said state of said end effector is a position of said movable portion.

31. A method for allowing a surgeon to control a robotic surgical apparatus as recited in claim 30, wherein:
a. said end effector is able to sense a force feedback for said movable portion; and
b. said sate of said end effector is an amount of force feedback for said movable portion.

* * * * *

UNITED STATES PATENT AND TRADEMARK OFFICE
CERTIFICATE OF CORRECTION

| | | |
|---|---|---|
| PATENT NO. | : 8,880,223 B2 | Page 1 of 1 |
| APPLICATION NO. | : 13/549622 | |
| DATED | : November 4, 2014 | |
| INVENTOR(S) | : Anil K. Raj et al. | |

It is certified that error appears in the above-identified patent and that said Letters Patent is hereby corrected as shown below:

Item [75] in the list of inventors on the title page, the inventor "Roger W. Carif" should be changed to "Roger W. Carff".

Signed and Sealed this
Twenty-eighth Day of July, 2015

Michelle K. Lee
*Director of the United States Patent and Trademark Office*